(12) United States Patent
Guck et al.

(10) Patent No.: US 6,631,290 B1
(45) Date of Patent: Oct. 7, 2003

(54) MULTILAYER CERAMIC ELECTRODES FOR SENSING CARDIAC DEPOLARIZATION SIGNALS

(75) Inventors: Beth Anne Guck, Blaine, MN (US); Adrianus P Donders, Founex (CH)

(73) Assignee: Medtronic, Inc., Minneapolis, MN (US)

( * ) Notice: Subject to any disclaimer, the term of this patent is extended or adjusted under 35 U.S.C. 154(b) by 141 days.

(21) Appl. No.: 09/696,365

(22) Filed: Oct. 25, 2000

(51) Int. Cl.$^7$ .............................................. A61B 5/04
(52) U.S. Cl. ........................ 600/509; 128/903; 607/28
(58) Field of Search ........................ 600/509, 517, 600/521, 508, 585, 484, 518, 529; 128/901, 902, 903; 607/4, 9, 17, 20, 28, 27, 60; 604/129, 891.1

(56) References Cited

U.S. PATENT DOCUMENTS

| | | | |
|---|---|---|---|
| 3,983,867 A | 10/1976 | Case | 128/2.06 G |
| 4,023,565 A | 5/1977 | Ohlsson | 128/2.06 B |
| 4,030,509 A * | 6/1977 | Heilman et al. | 607/4 |
| 4,082,086 A | 4/1978 | Page et al. | 128/2.06 E |
| 4,121,576 A | 10/1978 | Greensite | 128/2.06 V |
| 4,170,227 A | 10/1979 | Feldman et al. | 128/704 |
| 4,263,919 A | 4/1981 | Levin | 128/708 |
| 4,310,000 A | 1/1982 | Lindemans | 128/419 PG |
| 4,313,443 A | 2/1982 | Frosch et al. | 128/642 |
| 4,593,702 A | 6/1986 | Kepski et al. | 128/696 |
| 4,674,508 A | 6/1987 | DeCote | 128/419 PT |
| 4,729,376 A | 3/1988 | DeCote, Jr. | 128/419 PT |
| 5,331,966 A | 7/1994 | Bennett et al. | 128/696 |
| 5,345,362 A | 9/1994 | Winkler | 361/681 |
| 6,115,630 A * | 9/2000 | Stadler et al. | 600/521 |
| 6,230,059 B1 * | 5/2001 | Duffin | 607/60 |

FOREIGN PATENT DOCUMENTS

| | | | |
|---|---|---|---|
| WO | WO 94/08657 | 4/1994 | A61N/1/362 |
| WO | WO 99/06105 | 2/1999 | A61N/1/36 |
| WO | WO 99/42037 | 8/1999 | A61B/17/00 |
| WO | WO 00/57778 | 10/2000 | A61B/5/0452 |

* cited by examiner

Primary Examiner—Tu Ba Hoang
(74) Attorney, Agent, or Firm—Girma Wolde-Michael; Elisabeth L. Belden

(57) ABSTRACT

An implantable pacemaker is provided with cardiac depolarization sensing electrodes welded into the case along a peripheral edge surface thereof. The electrodes are coupled to signal processing circuitry within the case to provide leadless acquisition of electrocardiographic data for telemetry to a programmer. Each electrode is a thin film, multilayer ceramic structure mounted in a welding ring. Each electrode is substantially flat and is disposed within a recess in the peripheral edge surface of the case. Each electrode is a sandwich structure comprising a thin film layer, first and second ceramic layers, and a ground plane layer between the ceramic layers.

24 Claims, 8 Drawing Sheets

MULTILAYER CERAMIC ELECTRODES FOR SENSING CARDIAC DEPOLARIZATION SIGNALS

FIELD OF THE INVENTION

The present invention relates generally to implantable electrocardiographic data acquisition systems; and more particularly, it relates to a subcutaneous electrode used to sense, record, and acquire electrocardiographic data and waveform tracings from an implanted pacemaker without the need for or use of surface (skin) electrodes.

BACKGROUND OF THE INVENTION

The electrocardiogram (ECG) is commonly used in medicine to determine the status of the electrical conduction system of the human heart. As practiced, an ECG recording device is commonly attached to the patient via ECG leads connected to pads arrayed on the patient's body so as to achieve a recording that displays the cardiac waveforms in any one of 12 possible vectors.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) and the electrogram (EGM). The PQRST is an electrocardiogram representation of a waveform depicting P to be the depolarization process throughout the atria, QRS depolarization process throughout the ventricles, and T the repolarization of the ventricles. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available near or around the heart to pick up the depolarization wave front.

As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, however, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited, by mechanical problems and poor signal quality. Electrodes attached externally to the body are a major source of signal quality problems and analysis errors because of susceptibility to interference such as muscle noise, power line interference, high frequency communication equipment interference, and baseline shift from respiration. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

It is known in the art to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems that combine surface EKG signals for artifact rejection.

The primary use for multiple electrode systems in the prior art appears to be vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 issued to Page, et al., discloses a four electrode orthogonal array that may be applied to the patient's skin both for convenience and to ensure the precise orientation of one electrode to the other. U.S. Pat. No. 3,983,867 issued to Case describes a vector cardiography system employing ECG electrodes disposed on the patient in normal locations and a hex axial reference system orthogonal display for displaying ECG signals of voltage versus time generated across sampled bipolar electrode pairs.

U.S. Pat. No. 4,310,000 to Lindemans and U.S. Pat. Nos. 4,729,376 and 4,674,508 to DeCote, incorporated herein by reference, disclose the use of a separate passive sensing reference electrode mounted on the pacemaker connector block or otherwise insulated from the pacemaker case in order to provide a sensing reference electrode that is not part of the stimulation reference electrode and thus does not have residual after-potentials at its surface following delivery of a stimulation pulse.

Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG.

U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes located on the surface of the casing of an implanted pacemaker.

SUMMARY OF THE INVENTION

The present invention encompasses a subcutaneous multilayer ceramic electrode that is welded individually into three or four openings or recesses placed around the perimeter of an implanted pacemaker case. These electrodes are electrically connected to the circuitry of an implanted pacemaker to form a leadless Subcutaneous Electrode Array (SEA) for the purpose of detecting cardiac depolarization waveforms displayable as electrocardiographic tracings on a programmer screen when the programming head is positioned above an implanted pacemaker (or other implanted device) so equipped with a leadless SEA.

This invention is designed to replace existing externally mounted electrodes and electrode wires currently used on the leadless ECG implantable pacemaker, as described in U.S. Pat. No. 5,331,966 issued to Bennett. This previous device had electrodes placed on the face of the implanted pacemaker. When facing muscle, the electrodes were apt to detect myopotentials and were susceptible to baseline drift. The present invention minimizes myopotentials and allows the device to be implanted on either side of the chest by providing maximum electrode separation and minimal signal variation due to various pacemaker orientations within the pocket because the electrodes are placed on the perimeter of the pacemaker in such a way as to maximize the distance between electrode pairs.

Because the multilayer electrode is a complete functional component with its own hermetically attached weld ring, the electrode can be welded directly into the IPG casing. The use of this invention and the accompanying manufacturing process will eliminate the need for a compliant shroud and improve the cosmetics and handling of the implantable pacemaker during the implant procedure.

The spacing of the electrodes in the present invention provides maximal electrode spacing and, at the same time, appropriate insulation from the pacemaker casing due to the insulative properties of the welding rings into which the electrodes are placed. The electrode spacing around the pacemaker's perimeter maintains a maximum and equal distance between the electrode pairs. Such spacing with the three-electrode equal spacing embodiment maintains the maximum average signal due to the fact that the spacing of the three vectors is equal and the angle between these vectors is equilateral, as is shown in mathematical modeling. Such spacing of the electrode pairs also minimizes signal variation. An alternate three-electrode embodiment has the electrodes arranged so that the spacing of two vectors is equal and the angle between these vectors is 90°. Vectors in these embodiments can be combined to provide adequate sensing of cardiac signals (ECGs).

The present invention also allows the physician or medical technician to perform leadless follow-up that, in turn, eliminates the time it takes to attach external leads to the patient. Such timesavings can reduce the cost of follow-up, as well as making it possible for the physician or medical technician to see more patients during each day. Though not limited to these, other uses include: Holter monitoring with event storage, arrhythmia detection and monitoring, capture detection, ischemia detection and monitoring (S-T elevation and suppression on the ECG), changes in QT interval, and transtelephonic monitoring. The S-T segment represents S, the point at which the depolarization process ends and repolarization of ventricles crests at T. The QT interval represents the point at which depolarization process of the ventricles starts and repolarizatlon of the ventricles crests.

DETAILED DESCRIPTION OF THE DRAWINGS

Figure 1:
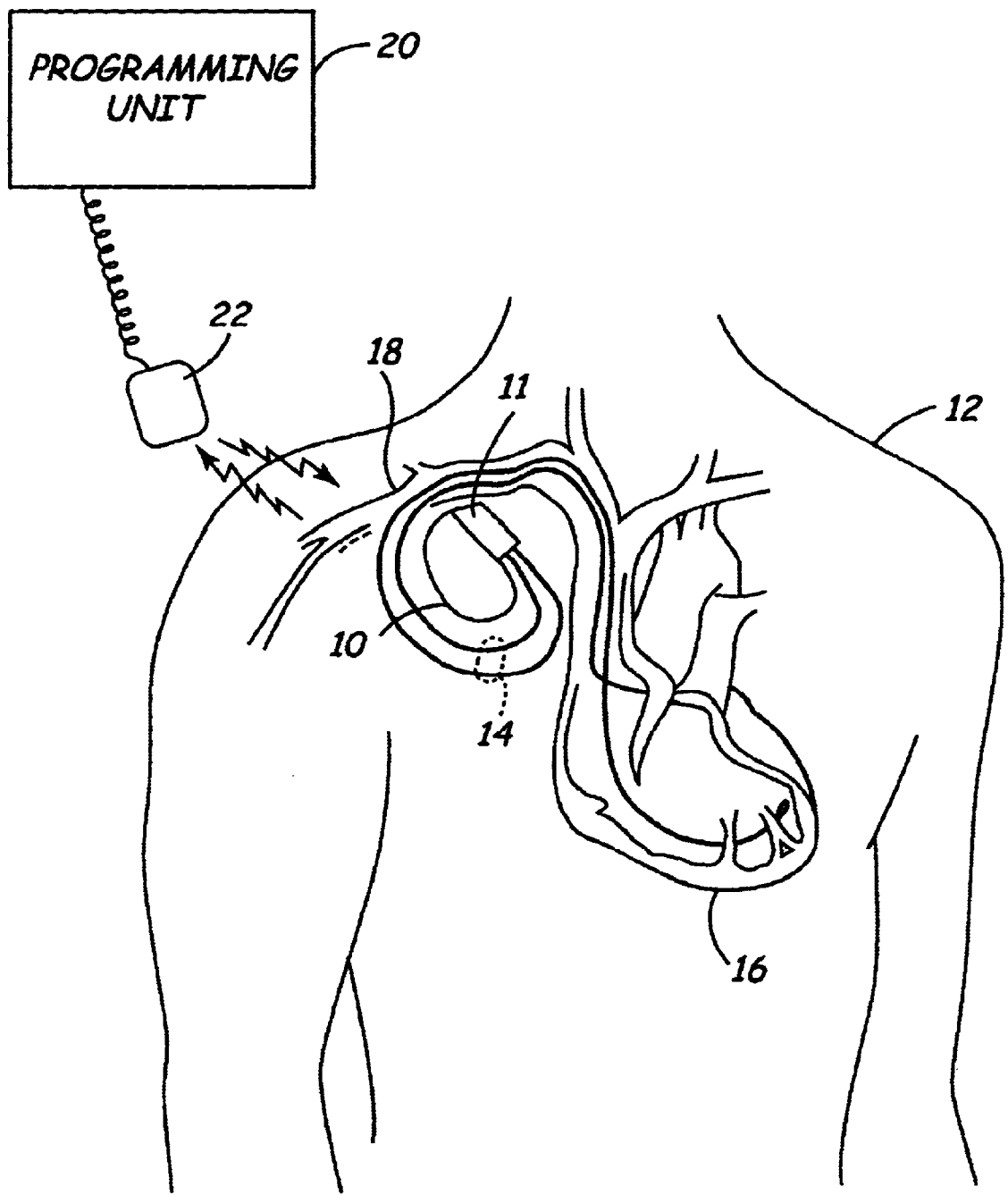
FIG. 1 is an illustration of a body-implantable device system in accordance with the present invention, including an implanted device in a patient and an external programming unit.

FIG. 1 is an illustration of an implantable medical device system adapted for use in accordance with the present invention. The medical device system shown in FIG. 1 includes an implantable device 10, a pacemaker in this embodiment, that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
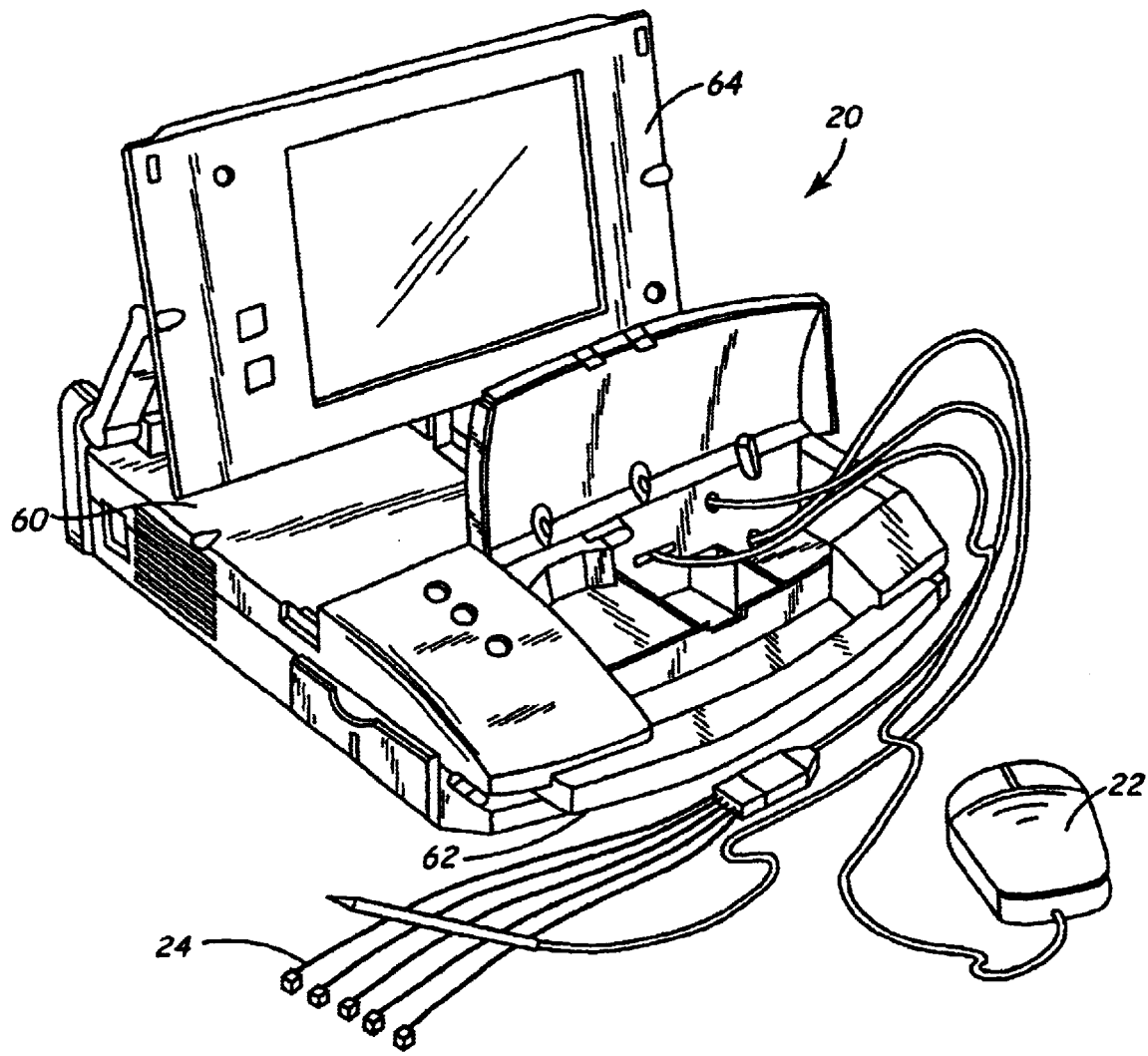
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory.

Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof. A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24. It is these leads that are rendered redundant by the present invention In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3A:
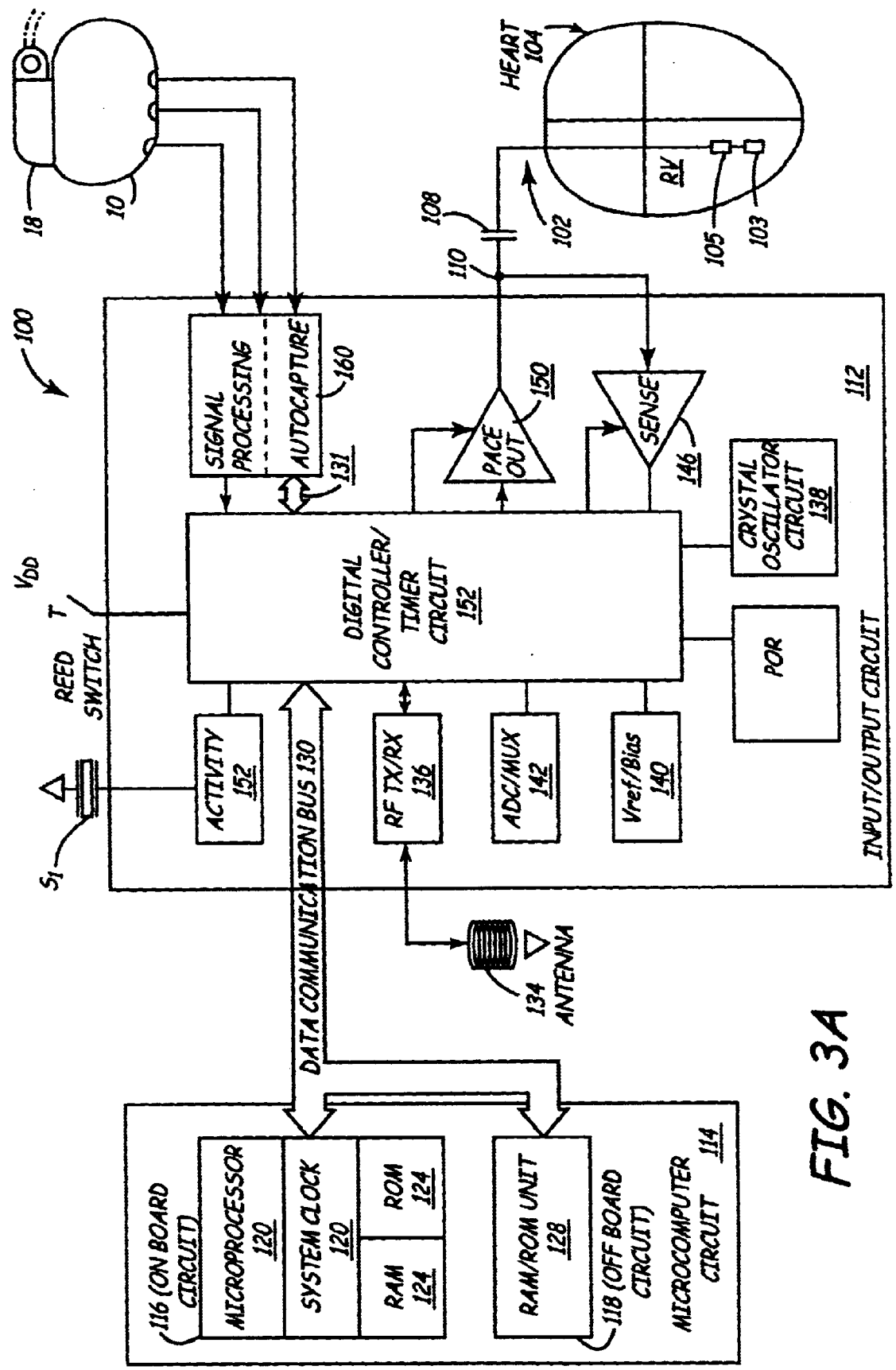
FIGS. 3A and 3B are block diagrams of the implanted device of FIG. 1.

FIG. 3A depicts a block circuit diagram illustrating a bradycardia pacemaker incorporating the concepts of the present invention. In the preferred embodiment of FIG. 3A, the pacemaker circuit 100 is schematically shown electrically coupled via a pacing lead 102 to a patient's heart 104. Lead 102 includes bipolar electrodes 103 and 105 at the distal end of lead 102 and positioned within the right ventricle (RV) of the patient's heart 104. Lead 102 can carry either unipolar or bipolar electrodes as is well known in the art. In the preferred embodiment, the lead 102 which couples pacemaker to the ventricular endocardium comprises a steroid-tipped electrode, bipolar lead. Electrodes 103 and 105 are coupled via suitable lead conductors through output capacitor 108 to node 110 and to input/output terminals of an input/output circuit block 112.

The input/output circuit 112 contains the operating input and output analog circuits for digital controlling and timing circuit 132 necessary for the detection of electrical signals derived from the heart, such as the R-wave and the far-field EGM, as well as for the application of stimulating pulses to the heart to control its rate under the control of software-implemented algorithms in a microcomputer circuit 114 and control and data signals traversing data buses 130 and 131.

Microcomputer circuit 114 comprises an on-board circuit 116 and an off-board circuit 118. On-board circuit 116 includes a microprocessor 120, a system clock 122, and on-board RAM 124 and ROM 126. Off-board circuit 118 includes an off-board RAM/ROM Unit 128. Microcomputer circuit 114 is coupled by data communication bus 130 to a digital controller/timer circuit shown at 132. Microcomputer circuit 114 may be fabricated of custom IC devices augmented by standard RAM/ROM components. It will be understood that the electrical components represented in FIG. 3A are powered by an appropriate implantable-grade battery power source (not shown).

An antenna 134 is connected to input/output circuit 112 for purposes of uplink/downlink telemetry through an RF transmitter/receiver circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier.

A crystal oscillator circuit 138, typically a 32,768 Hz crystal-controlled oscillator, provides main timing clock signals to digital controller/timer circuit 132. A Vref/bias circuit 140 generates a stable voltage reference and bias currents for the analog circuits of input/output circuit 112. An ADC/multiplexer circuit (ADC/MUX) 142 digitizes analog signals and voltages to provide telemetry and replacement time indicating function (EOL). A power-on-reset circuit (POR) 144 functions as a means to reset circuit and related functions to a default condition upon detection of a low battery condition, which will occur upon initial device power-up or transiently occur in the presence of electromagnetic interference, for example.

The operating commands for controlling the timing of the pacemaker depicted in FIG. 3A are coupled by bus 130 to digital controller/timer circuit 132 wherein digital timers set the overall escape interval of the pacemaker, as well as various refractory, blanking and other timing windows for controlling the operation of the peripheral components within input/output circuit 132.

Digital controller/timer circuit 132 is coupled to a sense amplifier (SENSE) 146 for receiving amplified and processed signals picked up from electrodes 103, 105 through lead 102 and capacitor 108 representative of the near-field electrical activity of the patient's heart 104. SENSE amplifier 146 produces a sense event signal for re-setting the escape interval timer within circuit 132. An output pulse generator 150 provides the pacing stimulus to the patient's heart 104 in response to a paced trigger signal developed by digital controller/timer circuit 132 each time the escape interval times out, or an externally transmitted pacing command has been received, or in response to other stored commands as is well known in the pacing art.

Digital controller/timer circuit 132 is coupled to a processing/amplifying circuit (ACTIVITY) 152 for receiving amplified and processed sensor output (Output$_{act}$) from sensor $S_1$ and associated ACTIVITY circuitry, which is representative of activity. In a preferred embodiment of the present invention, pacemaker 100 is capable of operating in various non-rate-responsive modes, which include VVI, VOO and YVT, as well as corresponding rate responsive modes of VVIR, VOOR and VVTR. Alternatively, the present invention may be implemented in a DDD/DDR pacing system where the PMT detection and recording features of the present invention may be implemented.

The system as envisaged in the context of the present invention includes the electrodes A, B and C coupled to the switching, signal processing and auto capture block 160 which is incorporated within the input/output circuit 112 and may include a far-field EGM recording system as well as the auto capture circuitry. Furthermore, it is contemplated that the processed EGM signals may be automatically recorded on the occurrence of certain events, particularly in conjunction with a dual chamber pacing or arrhythmia control system, for initiating the recording of the far-field EGM in the presence of PMTs, high atrial or ventricular rates or the detection of any other form of arrhythmia. The switching, processing and auto capture block 160 may take the form of the circuits depicted in FIG. 3B.

The detection of the capture of the patient's heart following the delivery of a stimulating pulse by the pace out circuit 150 may be conducted by selecting the highest peak amplitude EGM signal picked up between the electrodes A-B and C-B. The highest amplitude far field EGM signal may be employed to detect the capture of the heart by the pacing output pulse periodically in conjunction with the sequential decrementing of the pacing output pulse width or amplitude until capture is lost in a manner well known in the prior art. After capture is, lost, the output pulse energy may be incremented by a pre-set or percentage value.

Figure 3B:
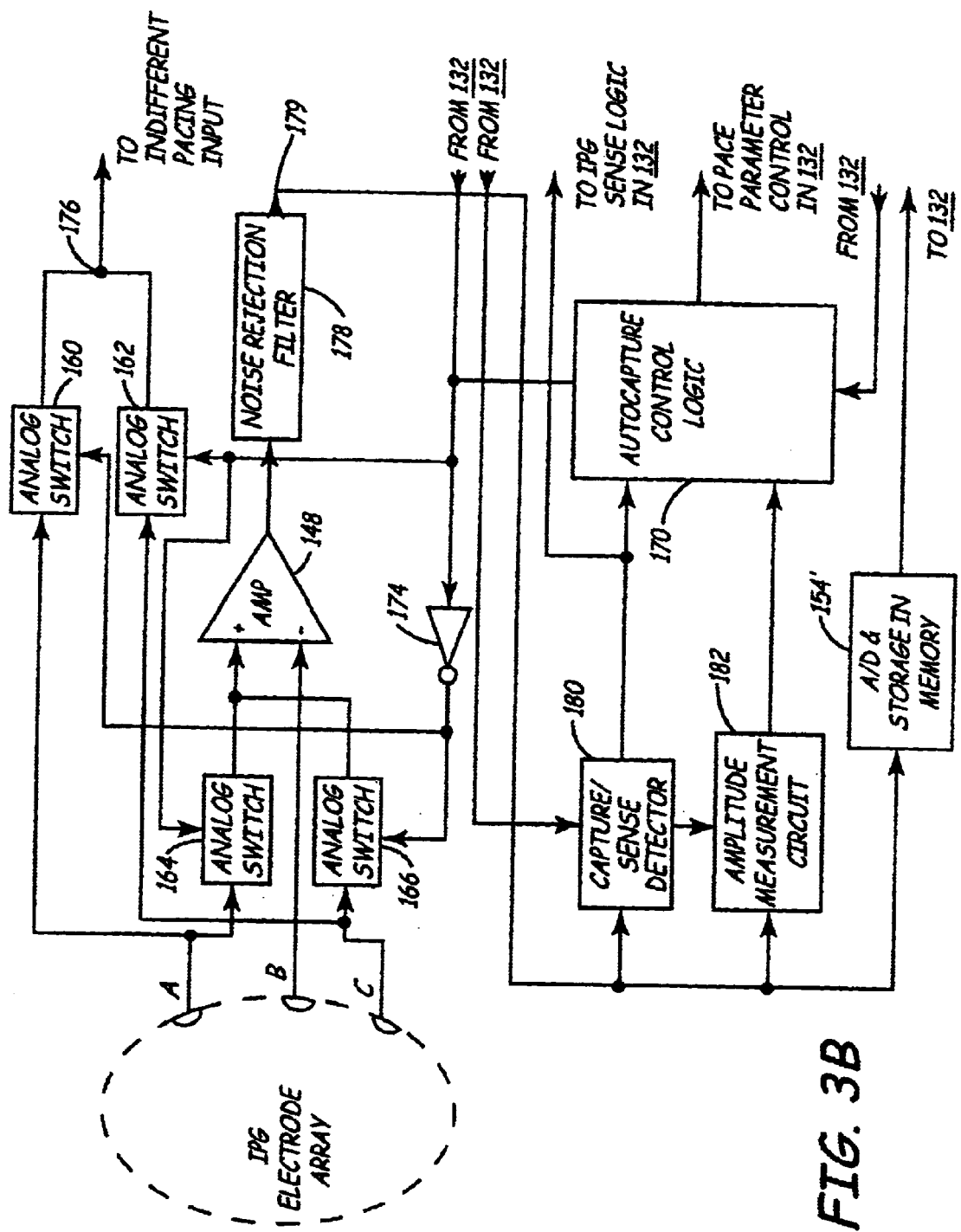

FIG. 3B depicts a block diagram of a system for detecting capture and setting the pacing pulse parameters accordingly, as well as a system for selecting one of the unused electrodes A or C as the pacing indifferent electrode in unipolar pacing systems. In FIG. 3B, the selection of the electrode pair A-B or C-B provides the directional far field EGM having preferred characteristics for subsequent use as the capture detect (and signal storage) EGM path and the dedication of the unused electrode as the classic unipolar pace/sense indifferent electrode. In FIG. 3B, the electrodes A, B and C are coupled to the block 160 of FIG. 3B, and the output signals of block 160 are applied to the digital controller/timer circuit 132. Certain control signals are received from circuit 132 to enable periodic testing of the optimum electrode pair and capture detection.

Further referring to FIG. 3B, the electrodes A, B and C are coupled to the inputs of analog switches 160, 162, 164 and 166 and the common electrode B is coupled to the negative input of the differential amplifier 148. The positive input of differential amplifier 148 is coupled to the output of analog switches 164 and 166, which are alternately selected by the autocapture logic 170. In effect, the autocapture logic 170, in response to command from the digital controller/timer circuit 132, provides a switch enable signal that is either a high or low binary signal to node 172. A high signal at 172 will be converted to a low signal by inverter 174 and applied to the switch control inputs of analog switches 160 and 166 to effectively open analog switches 160 and 166 to disconnect the electrode A from the node 176 and disconnect the electrode C from the positive input of differential amplifier 148.

Simultaneously, the switches 162 and 164 are closed by the high switch enable signal, thus connecting the electrode C to the node 176 and the electrode A to the positive input of differential amplifier 148. Whichever one of the electrodes A and C that is connected to node 176 operates as the pace/sense indifferent electrode. In bipolar pacing systems having electrodes 103 and 105 on lead 102 of FIG. 3A, it may be possible to program the pacing system to operate in either of the unipolar mode employing the electrodes A or C or the bipolar mode employing the ring electrode 105 as is well known in the prior art.

The output signal of the amplifier 148 is applied to the noise rejection band pass filter block 178 in order to filter out high and low frequency signal distortion induced by muscle noise and other artifacts. The output signal of the filter 178 is applied to the capture/sense detector 180 which may comprise a peak slope or amplitude threshold detector having programmable sensitivity threshold levels as is well known in the prior pacing art. The output signal of the capture/sense detector 180 is usually a fixed amplitude and duration pulse merely signifying the event detection. That sensed event signal may be applied directly to the digital controller/timer circuit 132 as well as to the autocapture logic 170.

The filtered directional electrogram signal may also be applied to the inputs of amplifier and signal processing block 182, as well as to the input of the analog to digital converter and temporary buffer memory storage block 154 to develop the digitized data representing the sampled amplitudes of the filtered directional EMG for data storage in RAM of circuit 114.

Figure 4:
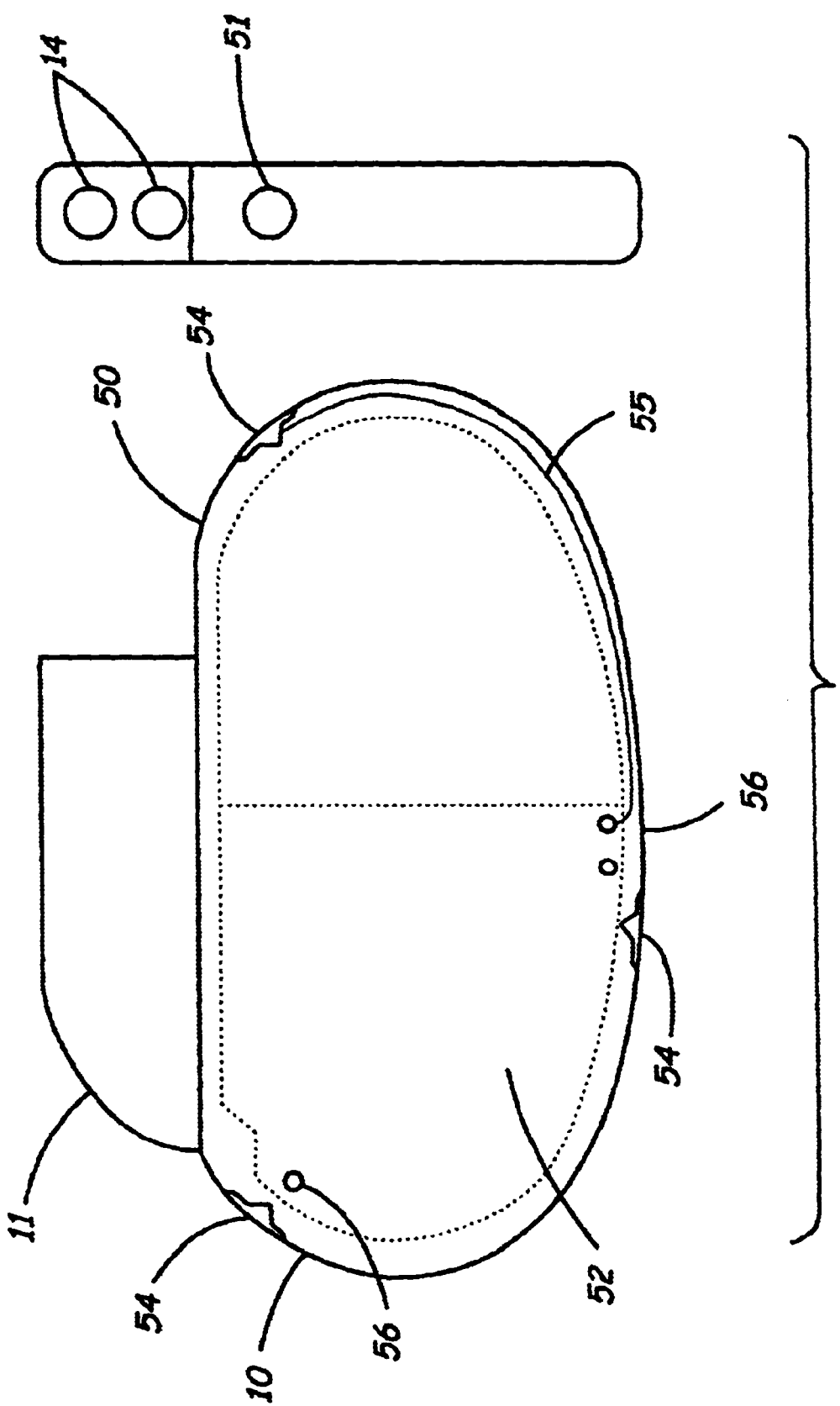
FIG. 4 is a cross sectional view of an implanted device in which the present invention may be practiced as a preferred embodiment.

FIG. 4 is a cross sectional view of implanted pacemaker 10 in which the present invention may be practiced as the preferred embodiment. The major components of pacemaker 10 consist of a hermetic casing in which are housed the electronic circuitry and a power source, in this case, a lithium-iodine battery. Lead connector module 11 provides an enclosure into which proximal ends of atrial and ventricular leads may be inserted into openings 14. Lead connector module is connected to pacemaker casing 10 and has electrical connections (not shown) between lead connectors and hermetic feedthroughs (also not shown).

Continuing with FIG. 4, multilayer ceramic electrodes 51 are welded into place on the flattened periphery of the pacemaker casing. In this preferred embodiment, the complete periphery of the pacemaker may be manufactured to have a slightly flattened perspective with rounded edges to accommodate the placement of flat electrodes such as those practiced in the present invention. Multilayer electrodes with feedthroughs 54 are welded to pacemaker casing (to preserve hermeticity) and are connected via wire 55 through pin 56 to the electronic circuitry.

Figure 5:
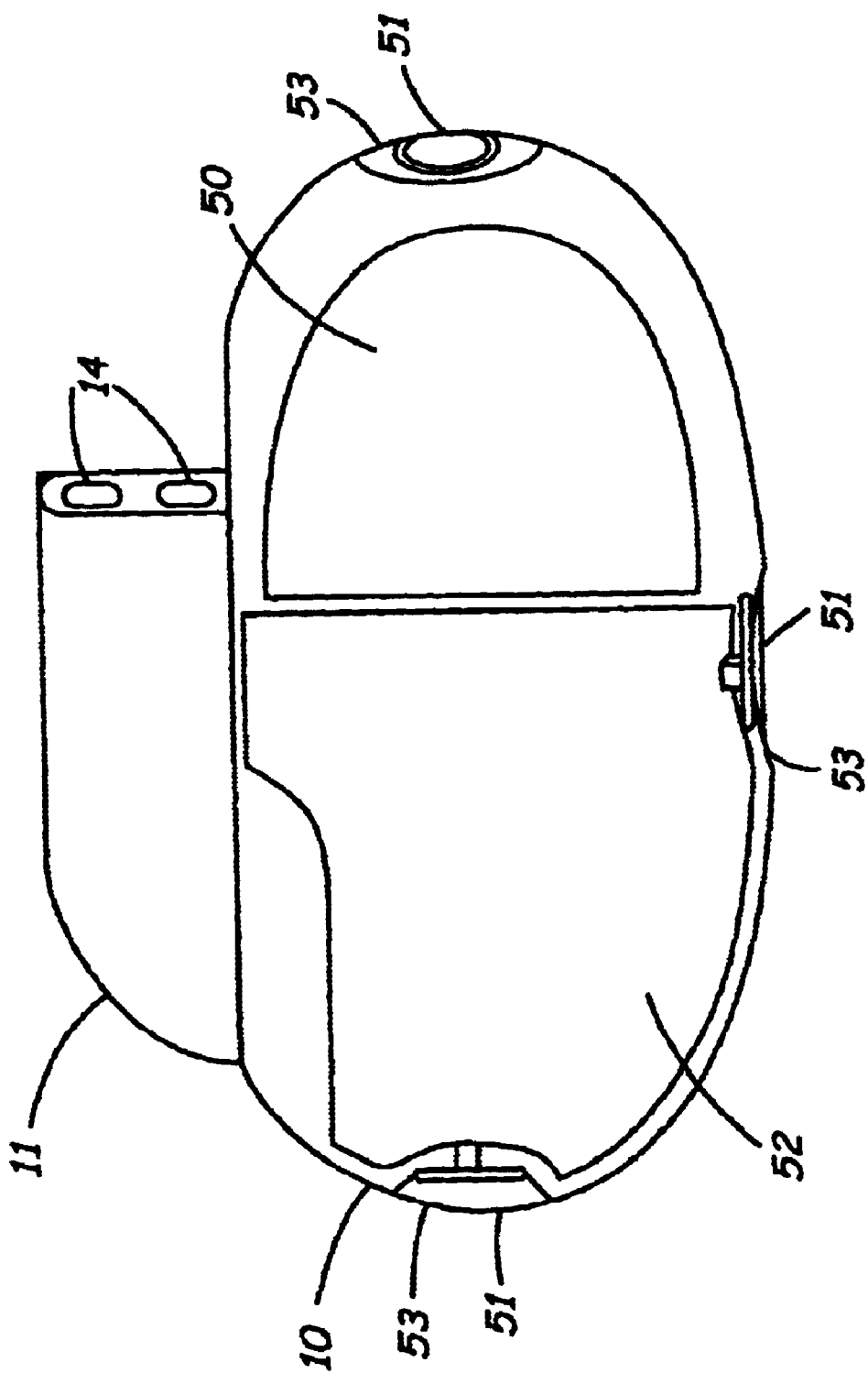
FIG. 5 is a perspective view of an implantable device in which the present invention may be practiced as an alternative embodiment.

FIG. 5 is a perspective view of implanted pacemaker 10 in which the present invention may be practiced as an alternative embodiment. The major components of pacemaker 10 consist of a hermetic casing in which are housed electronic circuitry and a power source, in this case, a lithium-iodine battery. Lead connector module 11 provides an enclosure into which proximal ends of atrial and ventricular leads may be inserted into openings 14. Lead connector module is connected to pacemaker casing 10 and has electrical connections between lead connectors and hermetic feedthroughs.

In this embodiment, multilayer ceramic electrodes 51 are welded into place on the periphery of the pacemaker casing. In this embodiment of the present invention, it is necessary to flatten and slightly depress the site 53 for electrode 51 to accommodate the flat specification of the present invention.

Figure 6:
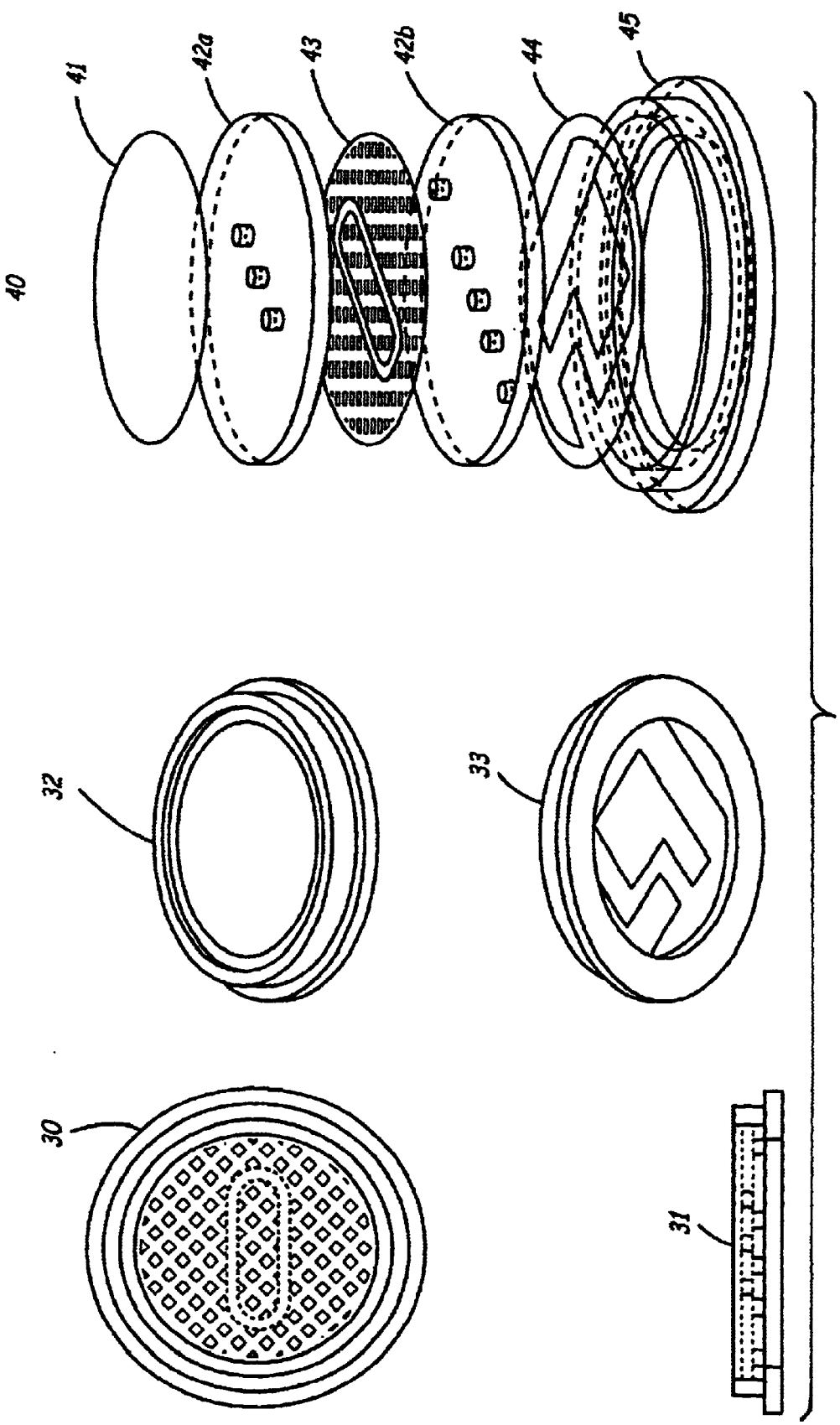
FIG. 6 shows both cross sectional and perspective views of the present invention.

FIG. 6 shows both cross sectional and perspective views of an electrode in accordance with the present invention. A cross sectional view from top 30 (with shadowed illustrations of the layers) and from side 31 of the present invention are depicted, as well as a top 32 and bottom 33 perspective views. An exploded perspective view 40 is depicted on the right side of FIG. 6.

In the preferred embodiment of this invention, thin film 41 may be used. Additional layers are: ceramic layer 42a, ground plane 43, ceramic layer 42b, and mini board 44, all of which are assembled within titanium welding ring 45.

The ceramic electrode 41 and associated metalizations are biocompatible and hermetic. Electrode metalizations, which serve as the signal-sensing surface, can be integrally bonded to the ceramic surface 42a. Electrode metalizations can be formed with thin film vacuum techniques, thick film techniques, combinations of thin and thick films, sintered metal powders, or by laser beam metalization coating techniques or spray techniques. Various metals and metal alloys can be used for the electrode surface 41 and are readily testable. The multi-layer ceramic electrode 40 can incorporate ground plane EMI (electromagnetic interference) shielding 43 and filter capacitor shielding placed integrally in its structure to form a monolithic unit. An alternative embodiment could provide for a surface mounted filter capacitor or a thin film capacitor deposited by vacuum means or a thick film capacitor material deposited by screen-printing or direct writing. Various biocompatible coatings can also be applied to the electrode to provide for additional hermetic barriers, eliminate inflammatory responses, and enhance electrode performance.

Continuing with FIG. 6, biocompatible, multi-layer ceramic surface 42a uses films or coatings (deposited by multiple processes and/or materials) for biocompatible electrode metalizations and corrosion protection. Multilayer ceramic electrode 40 serves as the means for signal inputs to implantable pacemaker 10. Multilayer ceramic electrode also provides EMI shielding and ready internal connectivity to the pacemaker's circuitry. Titanium weld ring 45, attached directly to the multi-layer ceramic electrode, grounds the electrode to the pacemaker's casing. The electrode's flat configuration and construction allows location of the electrode on any flat surface of the pacemaker (including distal mounting and edge mounting).

Electrode surface 41 can be enhanced by multiple means to improve ECG signal detection. The electrode surface can be platinized by electrolytic, electro less, or vacuum deposition techniques to increase and roughen the microstructure. Further, surface 41 can be modified by sintering of Pt micro spheres directly on the surface of the electrode. Because of the multi-layer nature of the electrode, a "well' or cavity with the thickness of one or more layers used to build the electrode can be fashioned to receive a filling of Pt micro spheres which can be sintered in the cavity. The sintered micro spheres can further receive a thin film platinization. Also, a steroid compound or disk can be intermixed with the micro spheres to minimize implant inflammation and improve electrode function. The well perimeter can be of any shape. The electrode metal sensing surface can be of various patterns regardless of techniques used to deposit the actual material. The surface pattern can be a solid circle, a spiral, cross hatching, concentric circles, concentric circles within each other, or a series of small circles. The surface pattern materials can be engineered to form three-dimensional features in the z-direction to appear as saw tooth, helical, or square-wave (in cross sectional view) surfaces with thicknesses of 0.002 to 0.005 inches. Further surface treatments can "decorate" these surfaces with even finer microstructure electrode materials to increase the total active surface area. The additional decoration or surface relief can be made with nano-sized Pt spheres, vacuum deposition techniques, or electrical means.

To improve the electrode response upon implant and to protect the electrode surface during the implant procedure, the surface of the bioelectrode can be treated with a wettable hydro gel or a sugar-coating that is deposited by dip, spray, or laser means. The protective layer would dissolve within a few days following implant.

The actual electrode materials include platinum, titanium nitride, iridium oxide, ruthenium oxide, gold, platinum black, or other suitable biocompatible electrode materials.

All connections from the electrode to the pacemaker circuitry are made by internal electrical connections (see FIGS. 4 and 5). The internal connections can be accomplished by any one of the following means: welding blocks or disks, laser connection of wires, welding, wire bonding, tab bonding, or solder attach.

Figure 7:
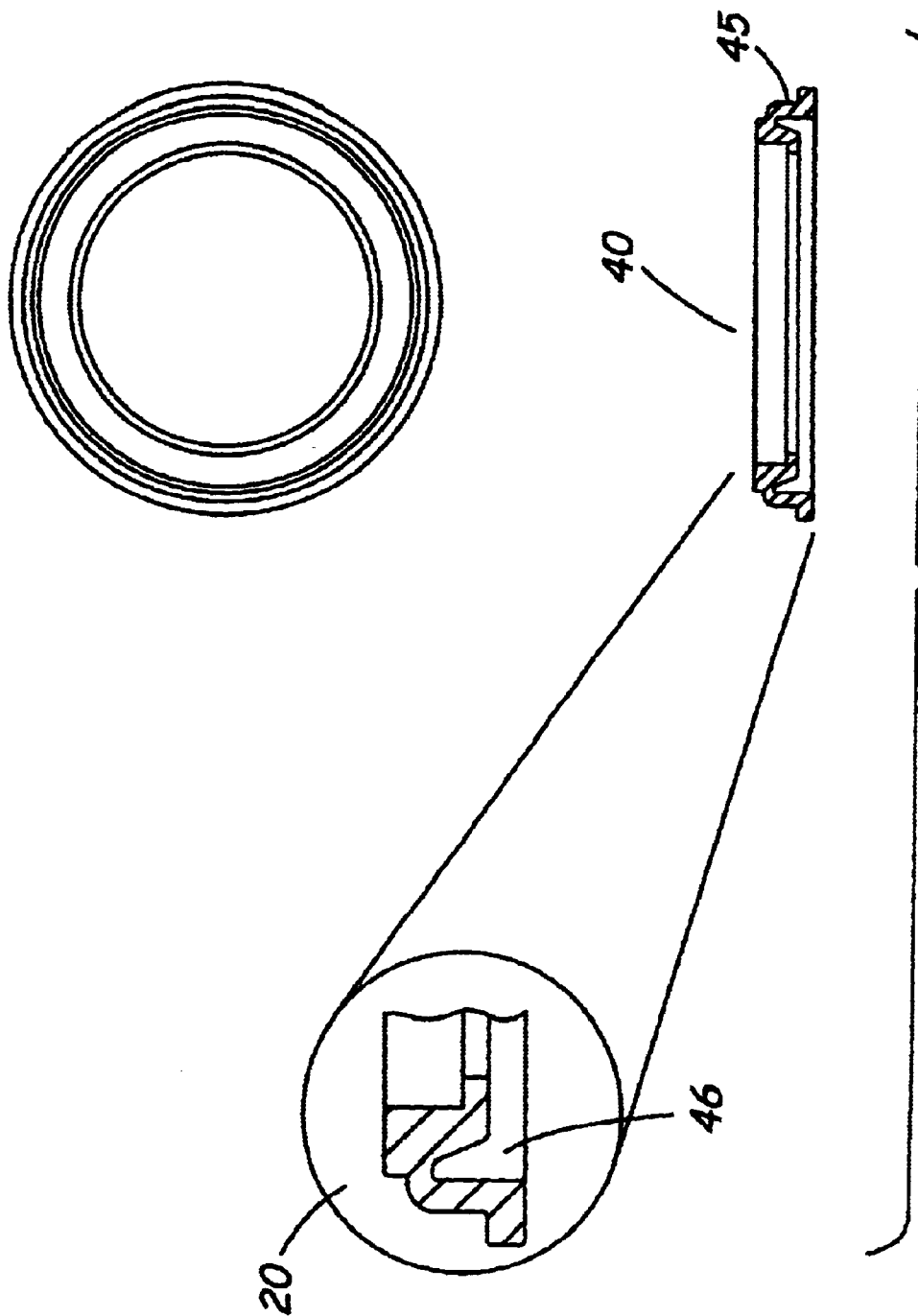
FIG. 7 is a cross sectional view of the construction of the present invention.

FIG. 7 is an illustration of the assembly of the present invention. Welding the electrode to such surfaces provides a hermetic seal. Welding ring 45 brazed to the electrode is designed with stress relief channel 46 to eliminate thermal and mechanical stress concentrations on the multi-layer ceramic during welding of the electrode into the IPG shield. In addition, the stress relief channel can accept coatings and compliant biocompatible materials to provide a redundant hermetic barrier for the electrode. Materials that can be used for the weld ring include: Grade 1 titanium, Grade 2 titanium, other unalloyed titanium for surgical implant according to ASTM F67; niobium, niobium-titanium alloys such as Niobium-46 titanium; Ti6Al4V; Ti5AI2.5Sn; Ti6A12CblTaI Mo; the alloy known as Tiadyne 3510 (35% Zr, 10% Nb, 55% Ti). Weld ring is attached to multi-later ceramic bioelectrode 40 with a brazing process that can be accomplished in a furnace with appropriate temperatures and atmospheres or with a laser micro joining process. Active braze materials can be used to eliminate the need to pre-metalize the ceramic edges for acceptable braze wetting. Braze materials include gold, gold alloys, and niobium alloys. Further, it is possible to attach the ceramic to weld ring 45 without any brazing process by using laser techniques to directly attach the two components to each other. A redundant hermetic barrier can be applied to the braze joint and to the specially designed holding channels in the weld ring structure. The hermetic barrier material is a dispensable epoxy. The sealing barrier can also be a vacuum-deposited thin film of biocompatible polymer, ceramic, metallic, or any combination thereof. Examples of barriers include diamond-like films, SiN, SiC, PTFE films. Parylene, titanium, glasses of various formulations, sapphire thin films, and naturally occurring sealants derived from various types of sea life.

While particular embodiments of the present invention have been shown and described, modifications may be made, and it is therefore intended in the appended claims to cover all such changes and modifications that fall within the true spirit and scope of the invention.

What is claimed is:

1. An implantable electrocardiographic data acquisition system for recording electrocardiographic data, the system comprising:

a hermetically sealed case;

an array of cardiac depolarization sensing electrodes attached to a peripheral edge surface of the case, each electrode being substantially flat and disposed within a depression in the peripheral edge surface of the case; and signal processing circuitry inside the case and electrically coupled to the array of electrodes to detect cardiac signals and record the electrocardiographic data.

2. The system of claim 1 wherein the periphery surface of the case is substantially flat.

3. The system of claim 1 wherein each electrode is a substantially flat, multilayer ceramic electrode.

4. An implantable electrocardiographic data acquisition system for recording electrocardiographic data, the system comprising:

a hermetically sealed case;

an array of cardiac depolarization sensing electrodes mounted in a periphery surface of the case; and signal processing circuitry inside the case and electrically coupled to the array of electrodes to detect cardiac signals and record the electrocardiographic data;

each electrode being a substantially flat, multilayer ceramic electrode of a sandwich structure mounted within a welding ring and comprising a thin film layer, first and second ceramic layers, and a ground plane layer between the ceramic layers.

5. An implantable electrocardiographic data acquisition system for recording electrocardiographic data, the system comprising:

a hermetically sealed case;

an array of cardiac depolarization sensing electrodes mounted in a periphery surface of the case; and signal processing circuitry inside the case and electrically coupled to the array of electrodes to detect cardiac signals and record the electrocardiographic data;

each electrode being a substantially flat, multilayer ceramic electrode mounted within a welding ring, and wherein each electrode is secured within a recess formed in the peripheral surface of the case by welding the ring to the case.

6. Apparatus for leadless acquisition of electrocardiographic data, comprising:

a hermetically sealed, implantable case;

an array of cardiac depolarization sensing electrodes disposed into the case along a peripheral edge surface, each electrode comprising a thin film, ceramic structure mounted in a welding ring.

7. The apparatus of claim 6 wherein each of the electrodes is a sandwich structure comprising a thin film layer, first and second ceramic layers, and a ground plane layer between the ceramic layers.

8. The apparatus of claim 6 wherein each of the electrodes is substantially flat and is welded into a recess formed in the peripheral edge surface of the case.

9. The apparatus of claim 6 wherein said ceramic structure is a multilayered composite.

10. The apparatus of claim 6 wherein said ceramic structure is biocompatible and hermetic.

11. The apparatus of claim 6 wherein said ceramic structure incorporates ground plane electromagnetic interference ("EMI") shielding and filter capacitor shielding.

12. The apparatus of claim 6, further comprising pacemaker pacing/sensing circuitry mounted within the hermetically sealed case.

13. The apparatus of claim 12, further comprising an antenna mounted within the hermetically sealed case to send and receive RF signals.

14. The apparatus of claim 12 wherein the array of electrodes comprises first (A), second (B) and third (C) electrodes.

15. The system of claim 14, further comprising:

means for detecting capture of a patient's heart following delivery of a stimulating pulse by selecting the highest peak amplitude electrocardiograph ("EGM") signal picked up between the first and second electrodes (A–B) and the third and second electrodes (C–B).

16. The system of claim 14, further comprising:

means for selecting one of the unused first (A) or third (C) electrodes as a pacing indifferent electrode for unipolar pacing.

17. The system of claim 6 wherein each electrode is brazed to a welding ring having a stress relief channel to eliminate thermal and mechanical stress concentrations on the electrode during attachment to the case.

18. The system of claim 17 wherein the stress relief channel has a coating of a biocompatible material to provide a redundant hermetic barrier for the electrode.

19. The system of claim 6 wherein each electrode comprises a stacked arrangement assembled within the welding ring, said stacked arrangement having a thin film layer, a first ceramic layer, a ground plane, a second ceramic layer, and a mini board.

20. The system of claim 6 wherein each electrode comprises an electrode sensing surface, said surface having a pattern selected from a group consisting of a solid circle, a spiral, cross hatching, concentric circles, and a series of small circles.

21. The system of claim 20 wherein the electrode sensing surface has a three-dimensional pattern feature in the z-direction selected from a group consisting of a saw tooth, a helix and a square-wave.

22. The system of claim 21 wherein the three-dimensional pattern feature has a thickness of 0.002 to 0.005 inches.

23. The system of claim 6 wherein the electrode materials are selected from a group consisting of platinum, titanium nitride, iridium oxide, ruthenium oxide, gold and platinum black.

24. An implantable electrocardiographic data acquisition system for recording electrocardiographic data, the system comprising:

a hermetically sealed case;

an array of cardiac depolarization sensing electrodes attached to a peripheral edge surface of the case, each electrode being substantially flat and countersunk substantially at the peripheral edge surface of the case; and signal processing circuitry inside the case and electrically coupled to the array of electrodes to detect cardiac signals and record the electrocardiographic data.

* * * * *